(12) United States Patent
Kelly et al.

(10) Patent No.: US 11,512,590 B2
(45) Date of Patent: Nov. 29, 2022

(54) GATHERING AND SEGREGATION OF HETEROGENEOUS CRUDE SOURCES

(71) Applicant: ExxonMobil Technology and Engineering Company

(72) Inventors: Francis X. Kelly, Skillman, NJ (US); J. Douglas Kushnerick, Warren, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 460 days.

(21) Appl. No.: 16/824,246

(22) Filed: Mar. 19, 2020

(65) Prior Publication Data
US 2020/0325773 A1 Oct. 15, 2020

Related U.S. Application Data

(60) Provisional application No. 62/831,783, filed on Apr. 10, 2019.

(51) Int. Cl.
| | |
|---|---|
| *E21B 49/08* | (2006.01) |
| *G01N 21/35* | (2014.01) |
| *G01N 33/28* | (2006.01) |
| *G05B 17/00* | (2006.01) |
| *G06Q 50/04* | (2012.01) |
| *G06Q 50/28* | (2012.01) |

(52) U.S. Cl.
CPC .............. *E21B 49/08* (2013.01); *G01N 21/35* (2013.01); *G01N 33/2823* (2013.01); *G05B 17/00* (2013.01); *G06Q 50/04* (2013.01); *G06Q 50/28* (2013.01)

(58) Field of Classification Search
CPC .... E21B 49/08; G01N 21/35; G01N 33/2823; G05B 17/00; G06Q 50/04; G06Q 50/28; G06Q 10/0832; G06Q 10/0633
See application file for complete search history.

(56) References Cited

U.S. PATENT DOCUMENTS

| | | | |
|---|---|---|---|
| 5,474,937 A * | 12/1995 | Anderson, II | G01N 33/1826 436/27 |
| 6,353,226 B1 * | 3/2002 | Khalil | A61B 5/1455 600/323 |
| 6,630,673 B2 * | 10/2003 | Khalil | A61B 5/1455 250/341.8 |
| 6,662,116 B2 | 12/2003 | Brown | |
| 7,523,647 B2 * | 4/2009 | Scott | G01N 22/00 73/32 R |
| 7,797,205 B2 | 9/2010 | Song et al. | |

(Continued)

*Primary Examiner* — Tung S Lau
(74) *Attorney, Agent, or Firm* — Vorys, Sater, Seymour and Pease LLP (57) ABSTRACT

Systems and methods are provided for gathering and segregation of oil extracted from a resource fields with a plurality of disparate sources in relatively close proximity. Instead of assigning a quality and/or destination for crude oil from an extraction source based on the origin of the crude oil, the crude oil can be characterized while still in local storage at or near the wellhead prior to transport to a refinery, a shipping or pipeline terminal, or another type destination for crude oil. Based on the characterization, one or more characteristics of the crude oil can be used to assign the crude oil to one of a plurality of destinations. The crude oil can then be transported to the assigned destination.

21 Claims, 2 Drawing Sheets

(56) References Cited

U.S. PATENT DOCUMENTS

| | | | | |
|---|---|---|---|---|
| 7,826,972 | B2* | 11/2010 | Babour | G01V 3/083 |
| | | | | 702/2 |
| 9,626,729 | B2* | 4/2017 | Phillips | G06Q 10/0875 |
| 2002/0084417 | A1* | 7/2002 | Khalil | G01N 21/49 |
| | | | | 250/341.8 |
| 2008/0238428 | A1* | 10/2008 | Babour | G01V 3/083 |
| | | | | 324/323 |
| 2011/0253642 | A1* | 10/2011 | Lundin | E02B 15/06 |
| | | | | 210/747.6 |
| 2016/0339452 | A1* | 11/2016 | Miller | G01N 27/22 |
| 2017/0097616 | A1 | 4/2017 | Cozad et al. | |
| 2017/0364795 | A1 | 12/2017 | Anderson et al. | |
| 2019/0102622 | A1* | 4/2019 | Spalenka | G06V 20/176 |

* cited by examiner

GATHERING AND SEGREGATION OF HETEROGENEOUS CRUDE SOURCES

CROSS REFERENCE TO RELATED APPLICATIONS

This application claims priority to U.S. Provisional Application Ser. No. 62/831,783 filed Apr. 10, 2019, which is herein incorporated by reference in its entirety.

FIELD

Systems and methods are provided for allocation of crude oil volumes generated from shale oil fields and other fields with high variability between wells.

BACKGROUND

Crude oil derived from shale sources is becoming an increasingly important source of petroleum. The Permian Basin and Bakken Shale are examples of shale oil fields. In contrast to conventional petroleum fields, shale oil fields can often include a large plurality of smaller wells. The output from these smaller wells is typically aggregated at a central location for delivery to a transport terminal, a refinery, or another type of destination for crude oil.

After aggregation, the destination for crude oil derived from a shale source can be determined in a manner similar to any other type of crude. For example, a crude can be analyzed to determine how the characteristics of an available crude match with the capabilities of a refinery. Conventionally, this can be accomplished by performing an assay of a sample from the crude source. A faster method for characterizing a crude source can be based on predicting some of the properties of a crude source based on spectroscopic analysis. An example of this type of characterization is provided in U.S. Pat. No. 6,662,116.

U.S. Patent Application Publication 2017/0097616 describes methods for hydrocarbon processing analysis. After modeling one or more refinery processes to determine optimized processing conditions, the analysis methods can provide improved understanding of how variations from the optimized processing conditions will impact refinery operation and/or profitability.

U.S. Pat. No. 7,797,205 describes a system for optimizing transport of crude oils and crude oil fractions from various sources/origin points to various destinations. The optimization is performed while including constraints related to commercial and physical limitations related to transport of crude oil and/or crude oil fractions using available transport methods, such as transport by ship. The optimization can allow crude oil and/or crude oil fractions from a variety of origination points to be matched with various potential destinations based on factors such as profitability, availability of transport, and availability of suitable storage.

SUMMARY

In an aspect, a method for transporting crude oil is provided. The method includes obtaining a sample of a crude oil associated with an extraction site from a plurality of extraction sites. The extraction site can include a stored amount of the associated crude oil. The plurality of extraction sites can be within a radius of 50 miles or less, such as a plurality of extraction sites corresponding to a shale oil field. A data fingerprint of the obtained sample of the associated crude oil can be generated, and a representation of the data fingerprint can be determined based on a plurality of known data fingerprints. One or more characteristic values for the associated crude oil can then be calculated based on the representation. The associated crude oil can be matched with a destination from a plurality of destinations based on the calculated one or more characteristic values. At least a portion of the stored amount of the associated crude oil can then be transported to the matching destination.

DETAILED DESCRIPTION

All numerical values within the detailed description and the claims herein are modified by "about" or "approximately" the indicated value, and take into account experimental error and variations that would be expected by a person having ordinary skill in the art.

Overview

In various aspects, systems and methods are provided for gathering and segregation of oil extracted from a resource fields with a plurality of disparate sources in relatively close proximity. Instead of assigning a quality and/or destination for crude oil from an extraction source based on the origin of the crude oil, the crude oil can be characterized while still in local storage at or near the wellhead prior to transport to a refinery, a shipping or pipeline terminal, or another type destination for crude. Based on the characterization, one or more characteristics of the crude oil can be used to assign the crude oil to one of a plurality of destinations. The crude oil can then be transported to the assigned destination.

Shale oil fields typically include a large plurality of extraction points. Although the extraction points are in relatively close proximity (such as within a radius of 50 miles or less, or 20 miles or less, or 10 miles or less), the characteristics of the extracted oil can vary significantly at each wellhead. In some instances, the quality at a single wellhead can vary significantly depending on the current depth of the well. The large variations in crude oil quality within a shale field are in contrast to the crude oil produced from a wellhead in a conventional oil field. In a conventional oil field, wells in relatively close proximity are expected to generate crude oils of similar characteristics.

In a shale oil field, the size of individual wells is also typically small. Due to the small size, it is not practical to generate a refinery scale volume of crude oil from an individual wellhead. Instead, based on economic considerations, the oil at an individual shale oil extraction site is typically stored in a storage tank associated with the extraction site. When a sufficient amount has accumulated, a tanker truck can then be used to transport the oil to a common storage area associated with a refinery, a transport terminal, or another suitable destination for a crude oil. Conventionally, the oil extracted from the various extraction points in a shale oil field is aggregated into the common storage area. The aggregated oil in the common storage area is then treated as a single source based on a characterization of the aggregated oil.

In contrast to a conventional aggregation strategy, in various aspects the accumulated oil at individual extraction sites can be characterized prior to transport (such as by tanker truck) to a destination with a common storage area.

By characterizing the oil prior to transport, the characterization can be used to select a destination from a plurality of destinations. The characterization can be performed by any convenient method that is suitable for performing characterization at a remote location. For example, infrared (IR) spectroscopy can be used to characterize the oil, such as by performing IR characterization at the extraction site using a portable spectroscopy unit or by transporting a sample of the oil to a central testing location.

The selection of a destination can be based on one or more characteristics of the crude oil. In some aspects, the one or more characteristics can be incorporated into the objective function for an allocation model. An optimized solution can then be determined for the objective function. The destination can correspond to the destination generated in the optimized solution.

In other aspects, the characteristics can be compared with quality profiles corresponding to a plurality of available destinations. In some aspects, a quality profile can be set in advance based on a standard profile associated with a destination. In other aspects, the quality profile of one or more destinations can be periodically updated based on optimization analysis one or more process trains at the destination. Additionally or alternately, the quality profile can also be updated based on oil already received at the destination. It is noted that other factors can also be considered, such as the availability of storage at the destination.

By segregating the oil extracted from different extraction sites, additional value can be generated. For example, crude oil from wellheads that is suitable for lubricant base oil production can be delivered to a different destination, so that production of high value lubricant products can be increased while reducing or minimizing the amount of challenged crude that is processed at a facility for lubricant base stock production. More generally, segregation can be performed between any convenient number of destinations, to allow for improvement or optimization of the destination for oil from each extraction point.

Technical Effect

The systems and methods described herein enable the extension of allocation and/or optimization models to nonconventional crude oil resource fields. This enables segregation of crude oil fractions from a single resource field so that the crude oil fractions can be better matched with corresponding destinations for processing.

Crude Characterization

In this discussion, a data fingerprint for a petroleum sample is defined as a multi-variate data set based on measured values derived from the petroleum sample. The measured values can be collected in a single measurement step, such as by generating a spectrum using a spectroscopic technique, or based on a plurality of measurements. In various aspects, the data fingerprint can have a sufficient number of data points to allow a representation of the data fingerprint to be formed as a linear combination of previously obtained data fingerprints, without having the representation correspond to an over-determined solution.

The crude oil from an extraction site can be characterized prior to selecting a destination for the crude oil. In various aspects, the characterization can correspond to a spectroscopic characterization. For example, IR spectroscopy can be used to generate a spectrum or "fingerprint" of a sample of the crude oil. After obtaining a spectrum, a representation of the spectrum can be created based on a linear combination of spectra from other, previously characterized crudes. Based on this fit to previously obtained spectra, the crude being characterized can be represented as a corresponding linear combination (including the same or similar coefficients) of the previously characterized crudes whose spectra contribute to the linear combination. The properties of the crude being characterized can then be approximated based on the blend of previously characterized crudes. Additionally or alternately, the characterization can correspond to analytical testing of any convenient characteristic or property of a crude oil. For example, the characterization to form a data fingerprint can potentially include determination of sulfur content, nitrogen content, API gravity, or other quantities that are not determined by spectroscopic methods.

More generally, any convenient type of spectroscopy or other analytical testing suitable for characterizing a crude sample can be used to generate a data fingerprint that can be fit to a linear combination of previously obtained data fingerprints. With regard to using spectroscopy to generate the data fingerprint, U.S. Pat. No. 6,662,116 describes a procedure for performing a virtual crude assay based on representing a spectrum of an unknown sample as a combination of spectra for previously characterized samples. As explained in U.S. Pat. No. 6,662,116, various improvements or modifications can be made to the linear combination of spectra used to fit the spectrum of the unknown sample. For example, one or more physical and/or chemical properties may be available for the crude being characterized. To the degree that the predicted value of such physical and/or chemical properties differ from the measured values, the combination of previously characterized crudes can be adjusted to result in a value for the physical and/or chemical properties that is closer to the measured value. For example, a representation based on a linear combination of previously characterized spectra can be adjusted to provide an improved match to measured values of boiling range, density at 15° C., kinematic viscosity (at 40° C., 50° C., 100° C., or another temperature), elemental content (such as sulfur content, hydrogen content, or carbon content), viscosity index of a lubricant boiling range portion, cetane index of a distillate boiling range portion, an aromatics content, a paraffin content, or another convenient value.

The representation of the data fingerprint for the crude sample can calculated in any convenient manner. For example, after obtaining a data fingerprint corresponding to an on-site spectrum for a crude sample using a portable spectrometer, the spectrum can be uploaded to a central location for calculation of a representation based on a linear combination of previously obtained spectra.

Segregation of Shale Crude Oils Based on Destination Quality Profile

In some aspects, the characterization of a crude sample can be used to match the crude sample with a quality profile for one of a plurality of destinations. The quality profile can be based on one or more predicted and/or measured characteristics of a crude oil based on the characterization, such as a plurality of predicted and/or measured characteristics.

In some aspects, the quality profiles can be relatively static, so that the quality profiles are not dependent on outside factors. For example, a first destination can correspond to a transport terminal for crude oils suitable for lubricant base oil product. Such a destination could have a quality profile that specifies one or more of an aromatics content less than a threshold value, a viscosity index for a lubricant boiling range portion greater than a threshold value, a density at 15° C. within a specified range, or other characteristics that may indicate suitability for lubricant base oil production. A second destination could correspond to a refinery configured for effective processing of heavy oils. Such a quality profile could have a quality profile that specifies one or more of a hydrogen content below a threshold value, a density at 15° C. greater a threshold value and/or an API gravity less than a threshold value, one or more features from a distillation profile, a sulfur content greater than a threshold value, or other characteristics that may indicate a heavy oil. In this simplified example, the third destination quality profile could correspond to an open or remainder profile, indicating that any crude oils not matching another profile are sent to the destination with the remainder profile.

In other aspects, one or more destinations, such as a plurality of destinations, can have a quality profile that varies over time. The variation in a quality profile can be based on one or more factors. One type of variation can be based on crude oils already received at the destination. Another type of variation can be based on the remaining available storage at the destination. A third type of variation can be due to a change in desired characteristics associated with the destination.

A quality profile for a destination will typically correspond to a (possibly open-ended) range of acceptable values for at least one characteristic of a crude oil. As crudes that match the quality profile are identified and delivered to the destination, the aggregated oil at the destination may have characteristics that are an improvement relatively to the minimum and/or maximum requirements for the refinery (or other destination). This can allow the quality profile for the destination to be relaxed, as less favorable crude oils can be blended into the existing aggregated oil (i.e., existing inventory) while still staying within the overall desired specifications for the destination. For example, an initial quality profile for a refinery destination can include a specification for sulfur of 2.5 wt % or less, based on a target sulfur specification at the refinery. If the initial deliveries to the destination have a lower sulfur content, at some point in time the aggregated oil at the destination may only have a sulfur content of 1.5 wt % or less (or some other threshold value). If a sufficient amount of oil is already present at the destination, such as 25 vol % or more of the destination capacity, or 50 vol % or more, or 75 vol % or more (such as up to 95 vol %), the quality profile can be relaxed with respect to sulfur content, as higher values of sulfur can be blended into the already aggregated oil while still achieving the target sulfur specification.

More generally, the value range for one or more characteristics in a quality profile can be relaxed or tightened based on crude oil that is already aggregated at a destination. It is noted that the initial value for a characteristic in the quality profile may differ from the underlying target specification at the destination. Thus, if the initial quality profile includes a value range that is broader than the target specification at the destination, a tightening of a value range in a quality profile could occur.

Another type of variation can also be based on the amount of oil accumulated at a destination. In some instances, there may be a greater amount of crude oil than expected that satisfies a quality profile for a destination. In this type of situation, as crude oils are aggregated at the destination, the storage volume at the destination may become limited relative to the amount of available crude oil volumes. In this type of situation, it may be desirable to tighten the quality profile to allow higher selectivity with regard to crude oil volumes that are matched to the destination. This can allow the highest value crude oils relative to the destination to still be delivered to the destination, as opposed to simply filling the storage at the destination with the first crude oil volumes that match a less restrictive profile.

Still another type of variation can be based on a change in desired crude slate for a refinery, such as due to a change in the crude slate that is considered "optimal" for the refinery. In many instances, the quality profile for a destination can be based on a desired input crude slate for a refinery. When a destination is associated with a refinery or other processing plant for processing of crude oil, the quality profile for the destination can be adjusted in order to improve and/or optimize operation of the refinery. One option for adjusting the quality profile can be an adjustment based on changes in other sources used in the crude slate. This type of adjustment can allow a refinery to take advantage of the variable qualities in a shale oil field to match changes in the remaining crudes in a crude slate.

Another type of adjustment to the quality profile can be based on modeling of one or more processes at the refinery to improve or optimize operations. In order to account for the multiple interactions present between and/or within processing trains for refining of hydrocarbons and/or hydrocarbon-based chemical production, a multi-variable model can be used to determine an optimized solution for an objective function, such as an objective function for maximizing the profit of one or more refineries; one or more process trains within a refinery; one or more chemical production plants; one or more process trains within a chemical production plant; or a combination thereof. Such an optimized solution can be used in a variety of ways. For example, when conventional crude oils are being purchased to form a crude slate for a refinery, an optimized solution can be used to identify the most favorable crude oils to purchase based on the current price of the available crudes. This can include accounting for how variations in the crude slate may alter refinery operating conditions as well as how resulting product quality may be impacted.

In various aspects, instead of using an optimized solution to identify an existing crude oil, an optimized solution can be used to determine a quality profile. By characterizing crude oils at individual well heads in a shale oil field (or another type of field with variable crude oil characteristics), crude oils can be selected that are favorable for use in a refinery. The quality profile for a destination refinery can be set based on crude oils that can improve or optimize refinery performance and/or profitability. For example, an optimized solution for a refinery and/or for one or more processes within a refinery can include information regarding which feed and/or process characteristics can have a substantial impact on refinery profitability. This can include feed characteristics that are beneficial for profitability and/or feed characteristics that are required for proper refinery operation. U.S. Patent Application Publication 2017/0097616 describes an example of modeling of refinery processes to provide such information. This type of information from an optimized solution can be used to set one or more value ranges in a quality profile for a refinery.

To model one or more hydrocarbon processing facilities and/or one or more processes within a hydrocarbon processing facility, a model can be developed to represent the various aspects of a facility and/or process that are believed to be relevant. In addition to setting up variables, coefficients, and constraints to represent the various processes within a facility (or facilities), a slate of input feeds and/or a slate of output products can also be specified. The slate of input feeds can include any crude oil and/or other hydrocarbonaceous feeds that might be used to form one or more streams within a hydrocarbon processing facility. The slate of output products can include both desired products (such as lubricants, fuels, chemicals) as well as side products or waste products (such as fuel gas, sulfur, coke). It is noted that a "product" such as sulfur might actually correspond to an additional cost for disposal as opposed to providing additional profit.

For models of facility operation (such as refinery operation), the scope of the model can correspond to a single facility or multiple facilities. Depending on the nature of the model, the model can capture costs and benefits related to a) the crude oils, crude oil slates, and/or other feed sources that are used as inputs for processing at one or more hydrocarbon processing facilities (e.g., refineries, chemical production plants) that are represented within a model; b) costs and benefits related to the operations of various processes within a model, including distillations, hydroprocessing, thermal (optionally catalyzed) processing, synthesis reactions, conversion reactions, separations and purifications, and/or other types of processes that occur within a hydrocarbon processing facility; and c) costs and benefits related to products formed from the hydrocarbon processing facilities, including both primary products, secondary or side products, and/or waste products (such as products that have a cost associated with disposal). Determining a solution to a model of facility operation can be used to indicate types of crude oil (or other input streams) to purchase for processing depending on the costs of the crude oil, the value of the resulting products, and/or any limitations of the facility (or facilities) in handling the input feeds.

For real-time optimization models, the scope of the model can correspond to one or more process trains within a hydrocarbon processing facility, such as a plurality of process trains that are related based on using overlapping portions of a feed, using overlapping equipment, and/or providing complementary products. A typical example of using overlapping portions of a feed are refinery processes that receive input feeds from a common distillation unit (such as an atmospheric or vacuum pipestill), so that modifying the distillation cut points to benefit a first process can also lead to a modification of the feed for a second process.

Segregation of Crude Oils Based on Optimization Model

Optimization models are used at a variety of levels within the overall lifetime of processing a crude oil. Some optimization models can focus on refinery level operation, while other optimization models can focus on delivery of crude oils to the proper refineries/other processing locations. Generally, the optimization models are based on optimization of an objective function based on total profit, with various variables and constraints to represent the crude oils, transport methods, and/or processes being modeled.

Models to optimize resource allocation can have some similarities to refinery models, but some of the variables and constraints can differ due to the different focus. U.S. Pat. No. 7,797,205 describes an example of a resource allocation model for transport of crude oils from origination points to destination points, such as based on transport by ship. Resource allocation models can complement refinery models. Refinery models can determine the crude properties that enhance refinery profitability. Such crude properties can then be used in a resource allocation model to match available crude oils with destinations for use of the crude oils.

The variable nature of shale oil fields can pose difficulties when attempting to represent shale oil fields in a resource allocation model. Resource allocation models are typically focused on refinery-scale amounts of crude oils. Such amounts are significantly larger than the amounts of crude oil available from a single shale oil well.

It has been discovered that resource allocation models can be modified to accommodate the small volume nature of shale oil wells, so that crude oils from individual wells can be segregated into desirable uses based on the model. This can be achieved by using the allocation model to optimize the addition of a new small crude oil volumes to existing crude oil resources. Thus, instead of treating crude oils as fixed resources in an optimization for allocating crude oils to destinations, the optimization model can build up the crude oil for use at a destination based at least in part on shale oil volumes as they become available.

As an example, when a shale oil volume becomes available, the available destinations for the shale oil volume can be identified. The allocation model can then determine the optimized allocation for the new shale oil volume, based on the how the new shale oil volume modifies the properties of the existing crude oil inventory at a destination relative to any constraints corresponding to minimum or maximum qualities for the crude oil inventory at a destination; and/or based on the constraint of how much storage volume remains at a destination. Depending on the aspect, the constraints related to both quality and remaining storage volume can differ from a conventional allocation model. It is noted that other constraints on the objective function can also be used. For example, the model can include constraints related to transport, so that if a limited number of vehicles are available for transport of shale oil volumes to destinations, the transport limitations can be included in the consideration of what the "optimized" destination is for each shale oil volume.

With regard to modification of the properties of the existing crude oil at a destination, modeling shale oil volumes can result in a different type of constraint than the constraints used for modeling of conventional sources. When modeling conventional sources in an allocation model, one set of constraints is that the conventional source should satisfy the minimum and/or maximum quality requirements at the destination. However, for modeling of shale resources, constraining the shale oil volumes to meet minimum and/or maximum quality requirements can be either too narrow of a constraint.

In various aspects, the optimized use of a shale oil volume is not dependent on whether an individual shale oil volume meets quality requirements. Instead, the optimized use depends on whether mixing the individual shale oil volume with the existing inventory meets quality requirements. Due to the small amount of a shale oil volume, this is a substantially different constraint. For example, if the existing inventory is far from a minimum or maximum boundary with respect to a given property, a shale oil volume that is well outside the boundaries for that property could be added based on other properties that are within the minimum/maximum boundaries. This is in contrast to modeling allocation of crude oils from traditional sources. For traditional sources, blending of crude oils could occur prior to delivery (such as within a holding volume in a ship), but the resulting blended crude oil would satisfy constraints within the model for minimum and/or maximum quality. By contrast, the constraints for a shale oil allocation model can focus on the inventory at the destination, so shale oil volumes outside of the minimum/maximum quality window for a destination can be delivered, so long as the resulting total inventory still satisfies the constraints.

A different type of constraint for the storage volume at a destination can also be beneficial in some aspects, so that the quality of shale oil volumes delivered to a destination increases as the storage volume at the destination approaches close to the maximum capacity. For example, in some aspects the characterization of a new shale oil volume can be performed at the time when an operator arrives to collect the volume for transport. In this type of situation, new shale oil volumes may be added to the model individually or only a few at a time. In such aspects, more shale volumes can become available relatively frequently, such as once per day or even once every few hours. In this type of scenario, it may be desirable to avoid having a destination become full based on optimization of currently available shale oil volumes, as even more favorable shale oil volumes may be available in the near future. To account for this, rather than simply having a hard volume constraint on the inventory at a destination, the volume constraint can include both a hard constraint at the physical limit, and a penalty function as the inventor approaches the volume limit. The presence of a penalty function would still allow shale oil volumes to be delivered to an inventory approaching the physical (hard) limit, but only if the profit from the optimized solution was sufficiently large to overcome the subtraction from the penalty function.

Example of Gathering and Segregation Environment

Figure 1:
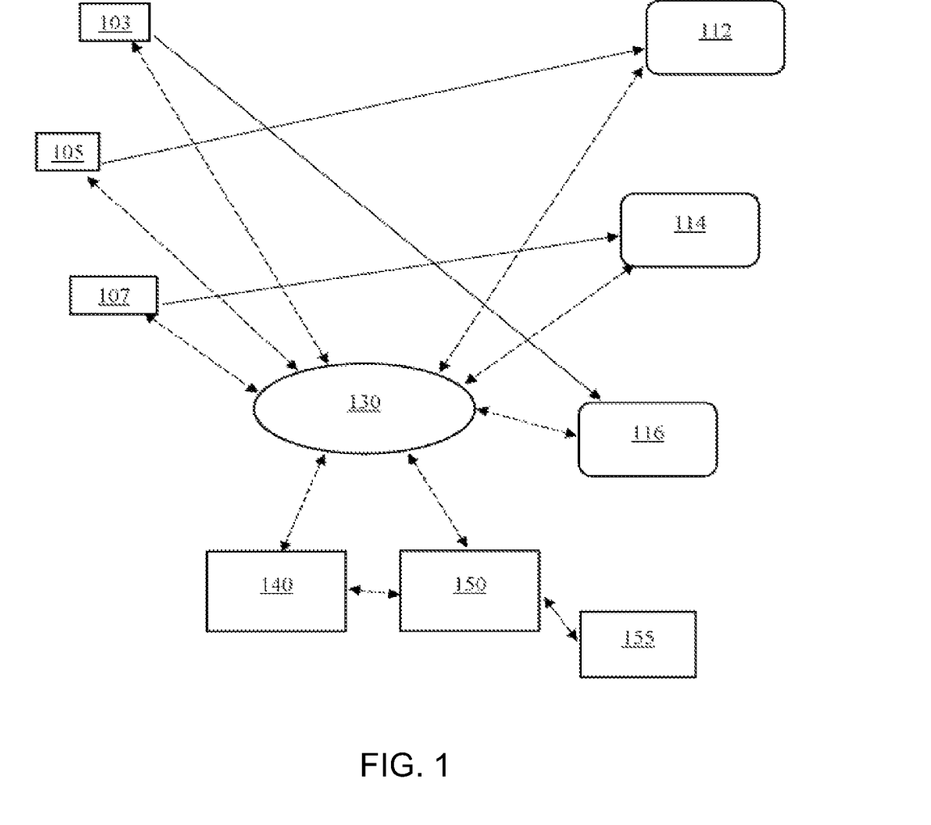
FIG. 1 shows an example of a computing network and crude oil transport environment suitable for use during gathering and segregating of crude oils from multiple production sites.

FIG. 1 shows an example of a network environment and a corresponding transport environment for gathering and segregation of crudes from multiple extraction sites. In FIG. 1, dotted lines represent network communications, such as communications over a local area network, a wide area network, or another convenient type of communication network. Solid lines represent transport of crude oil from an extraction site to a destination, such as a refinery or a transport terminal.

In FIG. 1, extraction sites 103, 105, and 107 represent extraction sites within a shale oil field or another resource field with variable quality over the range of the field. In the example shown in FIG. 1, characterization of crude oil associated with each extraction site is performed at the extraction site, and then uploaded via network 130 to virtual assay library 140. Alternatively, the characterization can be performed at a separate location (not shown). The characterization can correspond to performing spectroscopy on a crude oil sample to generate a spectrum.

The virtual assay library 140 generates a representation of a crude oil spectrum based on spectra for previously characterized crude oils. For example, virtual assay library 140 can determine a linear combination of a plurality of previously characterized crude oils to generate a representation of the spectrum for the crude oil sample. This virtual blend of previously characterized crude oils can then be used to make predictions regarding one or more characteristic values for the crude oil sample.

The one or more calculated characteristic values for the crude oil sample can then be passed to segregation scheduler 150. Segregation scheduler 150 can also receive quality profiles from destinations 112, 114, and 116, along with data regarding crude oils already received at each destination and remaining storage at each destination. The received quality profiles, current storage values, and available storage are stored in profile storage 155. When a representation is generated based on a crude oil sample from an extraction site (such as extraction site 103, 105, or 107), the segregation scheduler 150 can compare the characteristic values provided by the virtual assay library 140 with the quality profiles and available storage data in profile storage 155. Based on the comparison, the crude oil can be assigned to a destination (such as destination 112, 114, or 116). Optionally, segregation scheduler 150 can also update the quality profile for a destination based on the accumulated oil at the destination and/or the remaining available storage.

Assignment of Crude Oils to Destinations

The following is a prophetic example of how gathering and segregation can be performed by characterizing a crude oil prior to transport to a destination (e.g., refinery or transport terminal). In the following prophetic example, an illustration will be provided based on transport of oil from a single extraction site within a shale field over a period of time. It is understood that the methods in this example can be applied across a large plurality of extraction sites to allow for segregation of crude oils to different destinations. This example is based on segregation of crude oils based on quality profiles, as described above.

In this example, four potential destinations are available. The first destination has a quality profile based on suitability for lubricant production. The second destination corresponds to a pipeline terminal and has a quality profile based on suitability for a heavy oil refinery. The third destination has a quality profile based on low sulfur content. The fourth destination is a general destination, so that a crude oil that does not meet any of the other quality profiles is transported to the fourth destination.

At a first point in time, an operator visits the extraction site. A sample of the crude oil in the local storage for the extraction site is collected and provided to a central location for characterization. The characterization includes obtaining an IR spectrum for the sample and modeling the obtained IR spectrum using a linear combination of spectra from previously characterized samples. Based on the model representation, the crude sample is predicted to have a sulfur content of 1.5 wt % or less. The viscosity index of the lubricant boiling range portion is predicted to be 50. The density is predicted to be 0.90 g/cm$^3$. The hydrogen content is predicted to be 11.5 wt %.

The predicted/modeled values can be compared with the quality profiles for the various destinations. The quality profile for the first destination (refinery for lubricant production) is compared with the crude oil first, as it is the most restrictive quality profile. Of course, other factors could be used to determine the order for comparison of a crude oil with the possible quality profiles. The quality profile for the first destination includes a sulfur content of 2.5 wt % or less and a viscosity index for the lubricant boiling range portion of 50 or more. Because the crude oil matches with the quality profile, the crude oil is selected for transport to the first destination.

After transporting the contents of the local tank to the first destination, the extraction site continues to produce crude oil. After a period of time, an operator visits the site again and obtains a sample for characterization. The characterization indicates that the crude oil has not substantially changed.

The characterized values for the crude oil are then compared with the quality profile for the first destination. In the interim, a new optimized solution was developed for the refinery model for the refinery at the first destination. Based on the new optimized solution, the quality profile for the first destination has been updated to require a viscosity index of 60 or more for the lubricant boiling range portion. Because the crude oil characterization does not match the quality profile of the first destination, the crude oil characterization is compared with the second destination. The second destination corresponds to a heavy oil refinery. The operating advantage of the second destination is in efficient processing of challenged crudes. As a result, the quality profile for the second destination includes a density of greater than 0.92 g/cm³ and a hydrogen content of 11 wt % or less. The crude oil characterization also does not match the second quality profile. The third quality profile corresponds to a refinery with limited processing capabilities for removing sulfur. Therefore, the third quality profile corresponds to a sulfur content of 2.0 wt % or less. This matches the characterized values for the crude oil, so this batch of the crude oil is assigned for transport to the third destination.

After transporting the contents of the local tank to the third destination, the extraction site continues to produce crude oil. After a period of time, an operator visits the site again and obtains a sample for characterization. The characterization indicates that the crude oil has an increased sulfur content of 2.1 wt %, but is otherwise similar for the other specified properties.

The crude oil characterization still fails to match the first quality profile and the second quality profile. Previously, the crude oil characterization would have also failed to match the third quality profile, which would have resulted in assignment of the crude oil to the fourth (general) destination. However, in the interim, the third quality profile has been updated based on the oil already aggregated at the third destination. The oil already aggregated is well below the 2.0 wt % target, so the quality profile has been updated to allow 2.2 wt % sulfur or less. Based on the updated quality profile for the third destination, the crude oil characterization is a match. Therefore, the crude oil is assigned for transport to the third destination.

ADDITIONAL EMBODIMENTS

Embodiment 1

Figure 2:
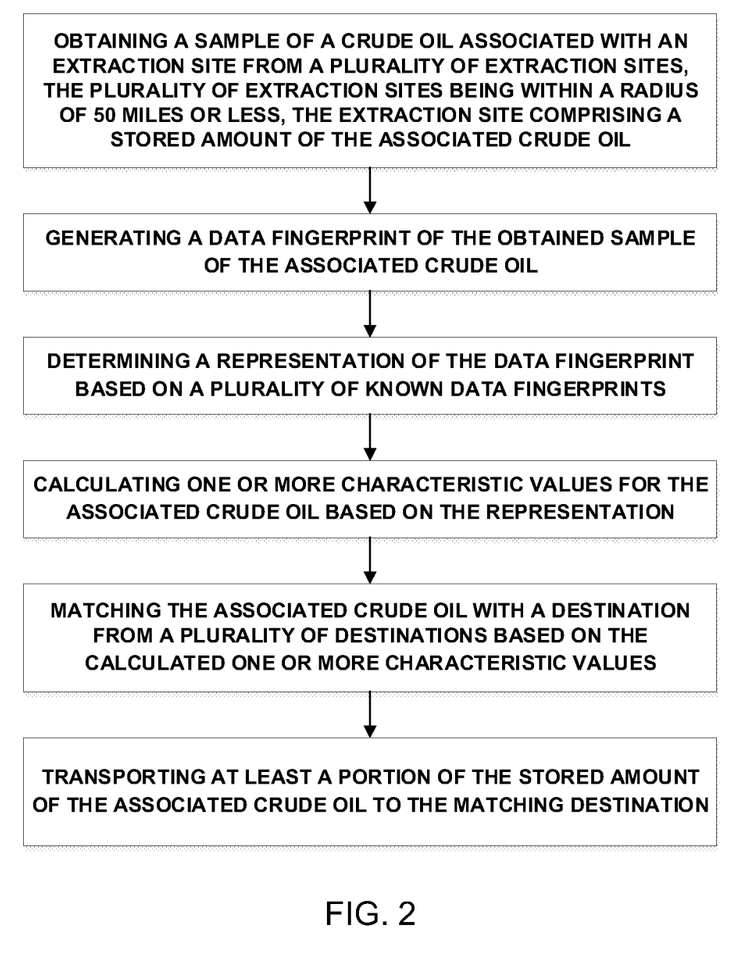

Referring now to FIG. 2, illustrated is a method for transporting crude oil, comprising: obtaining a sample of a crude oil associated with an extraction site from a plurality of extraction sites, the plurality of extraction sites being within a radius of 50 miles or less, the extraction site comprising a stored amount of the associated crude oil; generating a data fingerprint of the obtained sample of the associated crude oil; determining a representation of the data fingerprint based on a plurality of known data fingerprints; calculating one or more characteristic values for the associated crude oil based on the representation; matching the associated crude oil with a destination from a plurality of destinations based on the calculated one or more characteristic values; and transporting at least a portion of the stored amount of the associated crude oil to the matching destination.

Embodiment 2

The method of Embodiment 1, wherein generating a data fingerprint comprises performing a spectroscopic analysis on the obtained sample of the associated crude oil to generate a sample spectrum, and wherein the representation of the infrared spectrum comprises a linear combination of the plurality of known spectra.

Embodiment 3

The method of claim 2, wherein performing spectroscopic analysis comprises performing infrared spectroscopy to generate an infrared spectrum.

Embodiment 4

The method of any of the above embodiments, wherein generating a data fingerprint comprises performing a non-spectroscopic analysis on the obtained sample of the associated crude oil to generate one or more data points.

Embodiment 5

The method of any of the above embodiments, wherein matching the associated crude oil with a destination comprises incorporating the one or more characteristic values into an allocation model comprising an objective function, and matching the associated crude oil with a destination based on optimization of the objective function.

Embodiment 6

The method of Embodiment 5, wherein the allocation model comprises a penalty function associated with a destination storage volume, or wherein the allocation model comprises one or more constraints on a destination inventory, or a combination thereof.

Embodiment 7

The method of Embodiment 5 or 6, wherein the matched associated crude oil comprises at least one measured value, at least one characteristic value, or a combination thereof, that is outside of the one or more constraints on the destination inventory.

Embodiment 8

The method of Embodiment 7, wherein the at least one measured value comprises at least one measured value from the data fingerprint; or wherein the at least one characteristic value comprises at least one characteristic value from the calculated one or more characteristic values; or a combination thereof.

Embodiment 9

The method of any of Embodiments 1-4, wherein matching the associated crude oil with a destination comprises matching the one or more characteristic values with a quality profile corresponding to a destination from a plurality of destinations, a quality profile comprising one or more profile values.

Embodiment 10

The method of Embodiment 9, further comprising i) modifying at least one quality profile based on an available amount of storage volume at a corresponding destination; ii) modifying at least one quality profile based on one or more characteristic values of crude oil inventory accumulated at a corresponding destination; iii) modifying at least one quality profile based an optimized solution for an objective function for modeling one or more processes at a corresponding destination; or iv) a combination of two or more of i), ii), and iii).

Embodiment 11

The method of Embodiment 9 or 10, wherein at least one quality profile comprises a remainder profile.

Embodiment 12

The method of any of the above embodiments, the method further comprising: obtaining a second sample of a second associated crude oil from the extraction site, the extraction site comprising a second stored amount of the second associated crude oil, the second sample being obtained after the transporting of the at least portion of the stored amount of the associated crude oil; generating a second data fingerprint of the obtained second sample of the second associated crude oil; determining a representation of the second data fingerprint based on a plurality of known data fingerprints; calculating one or more second characteristic values for the second associated crude oil based on the representation of the second data fingerprint; matching the second associated crude oil with a second destination from the plurality of destinations based on the calculated one or more second characteristic values; and transporting at least a portion of the second stored amount of the second associated crude oil to the matching second destination.

Embodiment 13

The method of any of the above embodiments, wherein the extraction site comprises an extraction site in a shale oil field.

Embodiment 14

The method of any of the above embodiments, wherein the plurality of extraction sites are within a radius of 20 miles or less.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

The invention claimed is:

1. A method for transporting crude oil, comprising:
   obtaining a sample of a crude oil associated with an extraction site from a plurality of extraction sites, the plurality of extraction sites being within a radius of 50 miles or less, the extraction site comprising a stored amount of the associated crude oil;
   generating a data fingerprint of the obtained sample of the associated crude oil;
   determining a representation of the data fingerprint based on a plurality of known data fingerprints;
   calculating one or more characteristic values for the associated crude oil based on the representation;
   matching the associated crude oil with a destination from a plurality of destinations based on the calculated one or more characteristic values; and
   transporting at least a portion of the stored amount of the associated crude oil to the matching destination.

2. The method of claim 1, wherein generating a data fingerprint comprises performing a spectroscopic analysis on the obtained sample of the associated crude oil to generate a sample spectrum.

3. The method of claim 2, wherein performing spectroscopic analysis comprises performing infrared spectroscopy to generate an infrared spectrum.

4. The method of claim 3, wherein the representation of the infrared spectrum comprises a linear combination of the plurality of known spectra.

5. The method of claim 1, wherein generating a data fingerprint comprises performing a non-spectroscopic analysis on the obtained sample of the associated crude oil to generate one or more data points.

6. The method of claim 1, wherein matching the associated crude oil with a destination comprises incorporating the one or more characteristic values into an allocation model comprising an objective function, and matching the associated crude oil with a destination based on optimization of the objective function.

7. The method of claim 6, wherein the allocation model comprises a penalty function associated with a destination storage volume.

8. The method of claim 6, wherein the allocation model comprises one or more constraints on a destination inventory.

9. The method of claim 8, wherein the matched associated crude oil comprises at least one measured value, at least one characteristic value, or a combination thereof, that is outside of the one or more constraints on the destination inventory.

10. The method of claim 9, wherein the at least one measured value comprises at least one measured value from the data fingerprint; or wherein the at least one characteristic value comprises at least one characteristic value from the calculated one or more characteristic values; or a combination thereof.

11. The method of claim 1, wherein matching the associated crude oil with a destination comprises matching the one or more characteristic values with a quality profile corresponding to a destination from a plurality of destinations.

12. The method of claim 11, wherein a quality profile comprises one or more profile values.

13. The method of claim 11, further comprising modifying at least one quality profile based on an available amount of storage volume at a corresponding destination.

14. The method of claim 11, further comprising modifying at least one quality profile based on one or more characteristic values of crude oil accumulated at a corresponding destination.

15. The method of claim 11, further comprising modifying at least one quality profile based an optimized solution for an objective function for modeling one or more processes at a corresponding destination.

16. The method of claim 11, wherein at least one quality profile comprises a remainder profile.

17. The method of claim 1, the method further comprising:
   obtaining a second sample of a second associated crude oil from the extraction site, the extraction site comprising a second stored amount of the second associated crude oil, the second sample being obtained after the transporting of the at least portion of the stored amount of the associated crude oil;
   generating a second data fingerprint of the obtained second sample of the second associated crude oil;
   determining a representation of the second data fingerprint based on a plurality of known data fingerprints;
   calculating one or more second characteristic values for the second associated crude oil based on the representation of the second data fingerprint;
   matching the second associated crude oil with a second destination from the plurality of destinations based on the calculated one or more second characteristic values; and
   transporting at least a portion of the second stored amount of the second associated crude oil to the matching second destination.

18. The method of claim 1, wherein the extraction site comprises an extraction site in a shale oil field.

19. The method of claim 1, wherein the plurality of extraction sites are within a radius of 20 miles or less.

20. A method for gathering and segregating a plurality of crude oils, comprising:
- obtaining samples of crude oils associated with a plurality of extraction sites, the plurality of extraction sites comprising extraction sites in a resource field having a radius of 50 miles or less, each extraction site comprising a stored amount of the associated crude oil;
- generating, for each associated crude oil, a data fingerprint of the obtained sample;
- determining representations of the data fingerprints based on a plurality of known data fingerprints;
- calculating one or more characteristic values for each associated crude oil based on the representations;
- matching the associated crude oils with destinations from a plurality of destinations based on the calculated one or more characteristic values; and
- transporting at least a portion of the stored amount of each associated crude oil to the matching destination.

21. The method of claim 20, wherein the resource field comprises a shale oil field.

\* \* \* \* \*